United States Patent [19]
Held et al.

[11] Patent Number: 5,599,499
[45] Date of Patent: Feb. 4, 1997

[54] METHOD OF MICROWAVE STERILIZING A METALLIC SURGICAL INSTRUMENT WHILE PREVENTING ARCING

[75] Inventors: Jeffery S. Held, Chicago, Ill.; Robert F. Schiffmann, New York, N.Y.

[73] Assignee: Quiclave, L.L.C., Chicago, Ill.

[21] Appl. No.: 461,380

[22] Filed: Jun. 5, 1995

Related U.S. Application Data

[63] Continuation of Ser. No. 319,944, Oct. 7, 1994.

[51] Int. Cl.$^6$ .................... A61L 2/12; H05B 6/80
[52] U.S. Cl. ................ 422/21; 219/759; 219/762; 219/728
[58] Field of Search .................... 219/759, 762, 219/736, 728, 730, 710, 720; 422/21, 25

[56] References Cited

U.S. PATENT DOCUMENTS

| | | |
|---|---|---|
| 3,261,140 | 7/1966 | Long et al. . |
| 3,311,287 | 3/1967 | Long et al. . |
| 3,490,580 | 1/1970 | Brumfield et al. . |
| 3,494,722 | 2/1970 | Gray . |
| 3,961,569 | 6/1976 | Kenyon et al. . |
| 4,140,887 | 2/1979 | Sutton et al. . |
| 4,250,139 | 2/1981 | Luck et al. . |
| 4,316,070 | 2/1982 | Prosise et al. ............. 219/730 |
| 4,362,917 | 12/1982 | Freedman et al. .......... 219/730 |
| 4,398,077 | 8/1983 | Freedman et al. .......... 219/729 |
| 4,415,790 | 11/1983 | Diesch et al. . |
| 4,427,866 | 1/1984 | Pauly et al. . |
| 4,456,806 | 6/1984 | Arimatsu . |
| 4,503,307 | 3/1985 | Campbell et al. .......... 219/729 |
| 4,558,198 | 12/1985 | Levendusky et al. ....... 219/729 |
| 4,599,216 | 7/1986 | Rohrer et al. . |
| 4,614,514 | 9/1986 | Carr et al. . |

(List continued on next page.)

FOREIGN PATENT DOCUMENTS

| | | |
|---|---|---|
| 0152023 | 8/1985 | European Pat. Off. . |
| 2644698 | 9/1990 | France . |
| 1938110 | 3/1970 | Germany . |
| WO93/18798 | 9/1993 | WIPO . |

OTHER PUBLICATIONS

Pending U.S. patent application Ser. No. 08/595,743 Inventor(s): Schiffmann et al., filed on Feb. 2, 1996.
"Microwave Sterilization," Michael D. Rohrer et al., JADA, vol. 110, pp. 194–198, (Feb., 1985).
"Endodontic Obturation Technique," author unknown, Clinical Research Associates Newsletter, vol. 13, Issue 9, pp. 1–4, (Sep., 1989).
"Sterilization, Rapid Steam Heat," author unknown, Clinical Research Associates Newsletter, vol. 16, Issue 4, pp. 1–2, (Apr., 1992).
"Glimpses Given on Two Products," Robert Stevenson, Focus on Ohio Dentistry, vol. 66, No. 5, (May, 1992).
"Introducing Picotron" advertisement published by Park Dental Research Corp. Although the date of this reference is unknown, it is believed that the advertisement was available to the public prior to the filing of the above–mentioned application.

(List continued on next page.)

*Primary Examiner*—Philip H. Leung
*Attorney, Agent, or Firm*—Brinks Hofer Gilson & Lione

[57] ABSTRACT

The present invention concerns a container for preventing arcing of a metal object placed therein and subjected to microwave radiation. The surgical instrument container has a first surface having an exterior surface and a support surface and a second surface attached to the bottom having an exterior surface and an inner surface facing the first surface. The support surface and the inner surface define a volume of space into which the surgical instrument is placed therein. The inner surface has a microwave-to-heat transducer that absorbs microwave radiation impinging on the exterior surface of the second surface and converts the absorbed microwave radiation to radiant energy. The microwave-to-heat transducer also prevents substantially all of the microwave radiation impinging on the exterior surface of the second surface from entering the volume of space.

15 Claims, 4 Drawing Sheets

U.S. PATENT DOCUMENTS

| | | |
|---|---|---|
| 4,671,935 | 6/1987 | Rohrer et al. . |
| 4,786,773 | 11/1988 | Keefer ........ 219/720 |
| 4,808,782 | 2/1989 | Nakagawa et al. . |
| 4,808,783 | 2/1989 | Stenstrom . |
| 4,861,956 | 8/1989 | Courneya . |
| 4,933,525 | 6/1990 | St. Phillips ........ 219/720 |
| 4,952,420 | 8/1990 | Walters . |
| 4,956,155 | 9/1990 | Rohrer et al. . |
| 4,956,532 | 9/1990 | Koch . |
| 4,971,773 | 11/1990 | Rohrer et al. . |
| 5,019,344 | 5/1991 | Kutner et al. . |
| 5,019,359 | 5/1991 | Kutner et al. . |
| 5,039,495 | 8/1991 | Kutner et al. . |
| 5,061,443 | 10/1991 | Iijima et al. . |
| 5,108,701 | 4/1992 | Zakaria et al. . |
| 5,184,046 | 2/1993 | Campbell . |
| 5,185,506 | 2/1993 | Walters . |
| 5,217,768 | 6/1993 | Walters . |
| 5,254,821 | 10/1993 | Walters . |
| 5,256,846 | 10/1993 | Walters . |
| 5,281,784 | 1/1994 | Kuhn ........ 219/762 |
| 5,288,962 | 2/1994 | Lorence et al. ........ 219/730 |
| 5,300,746 | 4/1994 | Walters et al. . |
| 5,413,757 | 5/1995 | Kutner et al. . |
| 5,514,342 | 5/1996 | Corby et al. . |

OTHER PUBLICATIONS

"Ultraviolet/Ozone Generator for Sterilization of Medical and Dental Equipment," author unknown, published by East/West Technology Partners, Ltd. Although the date of this reference is unknown, it is believed that the article was available to the public prior to the filing of the above–mentioned application.

"Sterilization and Disinfection," Bernard L. Davis et al., source unknown, pp. 1452–1465. Although the date of this reference is unknown, it is believed that the chapter was available to the public prior to the filing of the above–mentioned application.

"Theory of Induction Heating," author unknown, source unknown, pp. 11–21. Although the date of this reference is unknown, it is believed that the chapter was available to the public prior to the filing of the above–mentioned application.

"Mitech Medical: Sterilizer Warms to World," Ellen Moffett, source unknown. Although the date of this reference is unknown, it is believed that the article was available to the public prior to the filing of the above–mentioned application.

Pending U.S. patent application Ser. No. 08/319,944, Filed On Oct. 7, 1994, Inventor: Held et al.

Pending U.S. patent application Ser. No. 08/381,685, Filed On Jan. 26, 1995, Inventor: Schiffmann et al.

Pending U.S. patent application Ser. No. 08/486,208, Filed On Jun. 7, 1995, Inventor: Schiffmann et al.

METHOD OF MICROWAVE STERILIZING A METALLIC SURGICAL INSTRUMENT WHILE PREVENTING ARCING

This application is a continuation of application Ser. No. 08/319,944, filed Oct. 7, 1994, (pending).

BACKGROUND OF THE INVENTION

1. Field of The Invention

This invention relates to a surgical instrument container that is exposed to microwave radiation and prevents arcing of a metallic surgical instrument placed therein, and sterilizes in a dry environment.

2. Discussion Of Related Art

The constant exposure of dental and medical personnel and instruments to saliva and blood in virtually every dental and medical procedure is an ever present hazard and potential contributor to the transmission of infection. A variety of approved instrument sterilization methods are available. However, all methods have drawbacks in relation to surgical instruments or dental handpieces and burs.

The most commonly used method of sterilization, autoclaving, is damaging for almost all high-speed dental handpieces. In a study of dental handpieces claimed to be autoclavable, deterioration of performance was noted in a simulated 3-month period. Furthermore, autoclaving, without pretreatment in an oil emulsion, will destroy the sharp edge of burs.

A second method of sterilization is to apply heat to the instruments. This method has the drawbacks that temperatures of about 160° C. are required while heat generators to rapidly produce such temperatures are not commonly available. The method has further disadvantages in that the rubber and plastic washers and bushings within the dental handpieces could potentially be damaged and long exposure times (approximately 1 hour) are needed.

Gas sterilization with an ethylene oxide mixture is acceptable for both handpieces and burs. However, this is impractical because of cost of equipment, long sterilization and aeration times involved, and cost of providing adequate protection for personnel.

Alkaline glutaraldehyde (2%) will sterilize equipment, but it must be used for 10 hours to kill spore-forming organisms or tuberculosis microorganisms and is irritating to tissue. It must also be constantly monitored as it is not effective when it is more than 2 weeks old.

Another method of sterilization of medical instruments is to scrub them in a detergent solution and wipe them with alcohol. However, because of their serrated or rough handgrip surfaces, most instruments cannot be disinfected in this way. Except when dry heat is available, no practical method exists for sterilization of dental burs that will not quickly dull the cutting edge.

Sterilization of dental and medical instruments by using microwaves directly and indirectly has been thought of as well. In U.S. Pat. Nos. 5,019,344; 5,019,359 and 5,039,495 it is disclosed to use microwaves to vaporize a liquid sterilant solution and to expose the instruments to either the vaporized sterilant alone or to both the microwaves and the vaporized sterilant. When using microwaves to sterilize the instruments, the instruments are placed in a shielded and pressurized atmosphere produced by the vaporized sterilant. The pressurized atmosphere prevents arcing and aids in sterilizing the instruments in conjunction with the microwaves.

In another microwave sterilization technique, dental instruments are directly exposed to microwaves within a microwave oven. The instruments may be placed in plastic autoclave bags when exposed. This technique suffers from several shortcomings, such as (1) needing to rotate the objects in a three-dimensional manner within the oven to uniformly heat the instrument; (2) needing to shield the oven from energy not absorbed by the instruments that is reflected back to the oven; and (3) requiring either an absorber of microwaves, such as water, or an absorber of radar waves within the oven to prevent arcing.

SUMMARY OF THE INVENTION

The present invention concerns a container, such as a surgical instrument container, for preventing arcing of a metal object, such as a metallic surgical instrument, placed therein and subjected to microwave radiation. The surgical instrument container has a first surface having an exterior surface and a support surface and a second surface attached to the first surface having an exterior surface and an inner surface facing the first surface. The support surface and the inner surface define a volume of space into which the surgical instrument is placed therein. The inner and/or the support surface has a microwave-to-heat transducer that absorbs microwave radiation impinging on the exterior surface of the second surface and converts the absorbed microwave radiation to radiant energy. The microwave-to-heat transducer also prevents substantially all of the microwave radiation impinging on the exterior surface of the second surface from entering the volume of space.

The present invention provides many advantages such as allowing one to inexpensively and quickly sterilize one or more metallic and non-metallic dental and/or surgical instruments.

The present invention allows one to safely place a metallic object within a microwave source or oven without producing arcing problems.

The present invention allows one to uniformly sterilize in a dry state in an electromagnetic environment.

The foregoing features and advantages of the present invention will be further understood upon consideration of the following detailed description of the invention taken in conjunction with the accompanying drawings, in which:

DESCRIPTION OF THE PREFERRED EMBODIMENT

Figure 1:
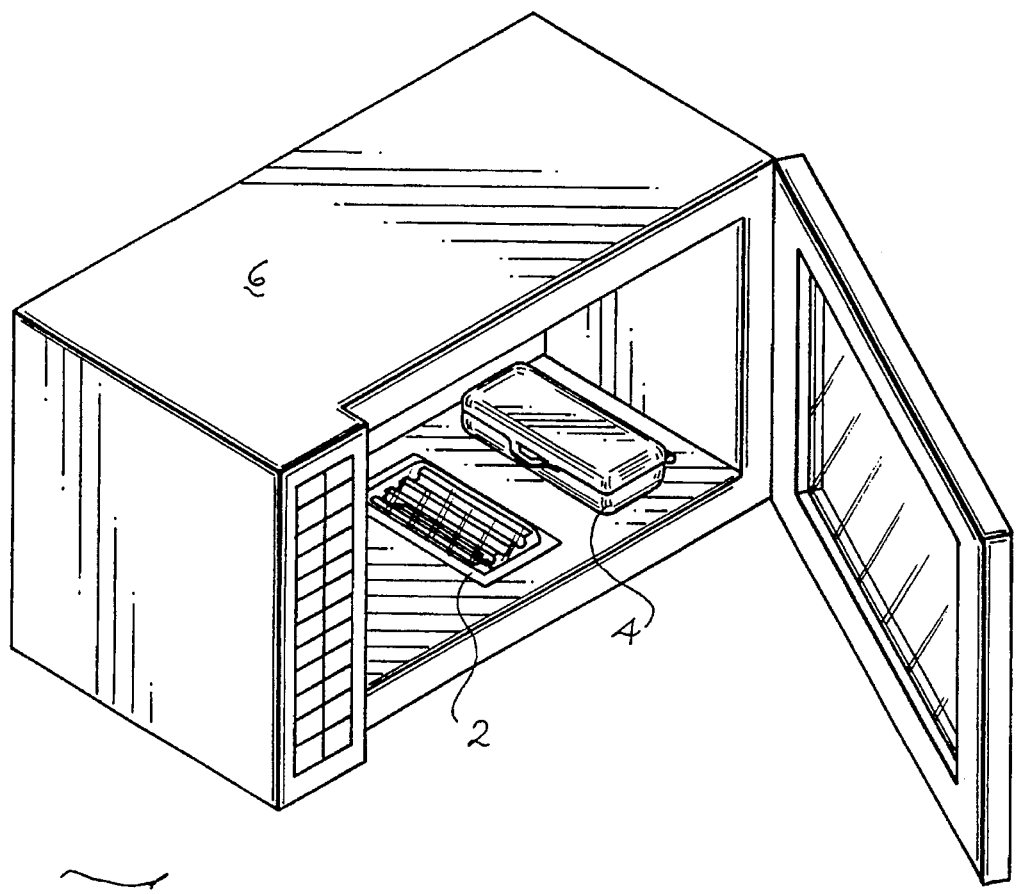
FIG. 1 shows a both a surgical instrument bag and cassette containing a surgical instrument that are placed in a microwave device for sterilization according to the present invention.

Referring now to the drawings wherein like reference characters designate identical or corresponding parts throughout the several figures, and in particular FIG. 1 that shows a pair of flexible or rigid surgical instrument containers such as bag 2 and cassette 4 are positioned within a microwave radiation generator, such as a microwave oven 6. Each of the containers 2, 4 contain metallic objects, such as surgical and/or dental instruments 8. As will be explained in detail below, the containers 2, 4 are designed to prevent arcing of the metallic surgical instruments placed therein due to the microwave radiation produced by microwave oven 6.

Figure 2:
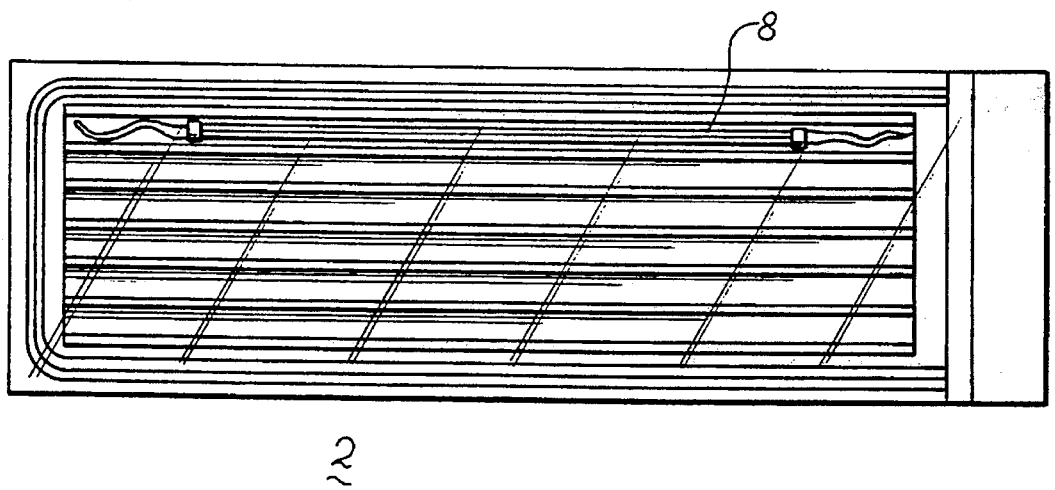
FIG. 2 shows a top view of the surgical instrument bag of FIG. 1.
Figure 3:
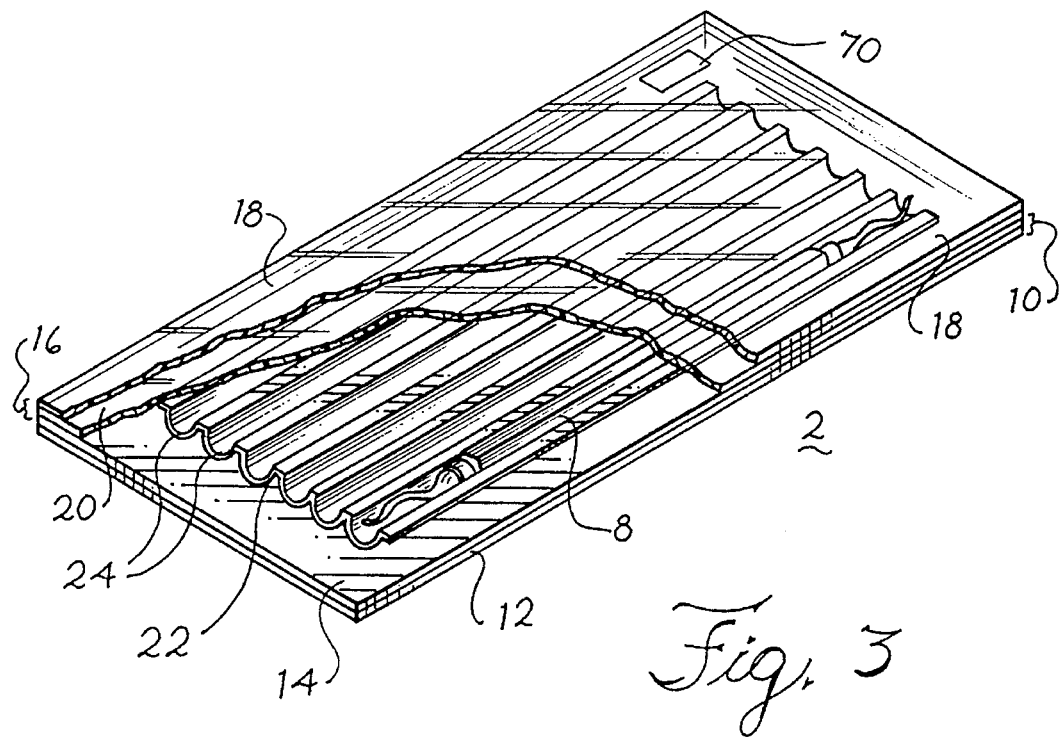
FIG. 3 shows a partially cut away view of the surgical instrument bag of FIG. 2.

Surgical instrument bag 2 is shown in FIGS. 2 and 3. Bag 2 preferably consists of a continuous surface having an inner surface defining a volume of space into which the surgical instrument 8 is placed therein. The continuous surface preferably has a bottom 10. The bottom 10 may be made of a single material such as a flexible aluminum foil or preferably has a dual layer structure with an exterior surface 12 and a support surface 14 as seen in FIG. 3.

The bag 2 also has a top 16 attached to bottom 10 that has an exterior surface 18 and an inner surface 20 facing the support surface 14. Exterior surface 18 preferably is made of a clear plastic material in conjunction with a perforated metal layer so that one can see the instruments 8 placed within bag 2. Such a structure allows viewing while at the same time preventing the microwaves from penetrating through the surface. Such a structure is well known in the art. Exterior surface 12 may also be made of a non-transparent plastic or paper. A surgical instrument 8 is placed within a volume of space defined by the support surface 14 and the inner surface 20. The bag 2 is then placed in the microwave oven 6 and exposed to microwaves.

Though it is well known that microwaves reflect off metals, they actually penetrate the metal surface by about 1μm. This slight penetration causes an activation of the surface electrons in a random manner and creates a current moving along the surface. If a potential charge builds up on a material to the level where it exceeds the ability of the air to carry away the charge, an arc will occur. It is well known that the build up of charge is particularly prevalent at sharp edges or points of the metal surface. This arcing can damage both the oven and the metallic instrument therein.

To help prevent arcing between metal surgical instruments placed in the volume of space of bag 2, the instruments 8 are preferably placed on a tray 22 that is positioned on support surface 14. As seen in FIG. 3, tray 22 is rectangular in shape, is made of paper or plastic and has one or more rectangular or round channels or compartments 24 in which a single instrument 8 is placed therein. By separating the instruments a sufficient distance from each other, arcing between the instruments is lessened.

Figure 7:
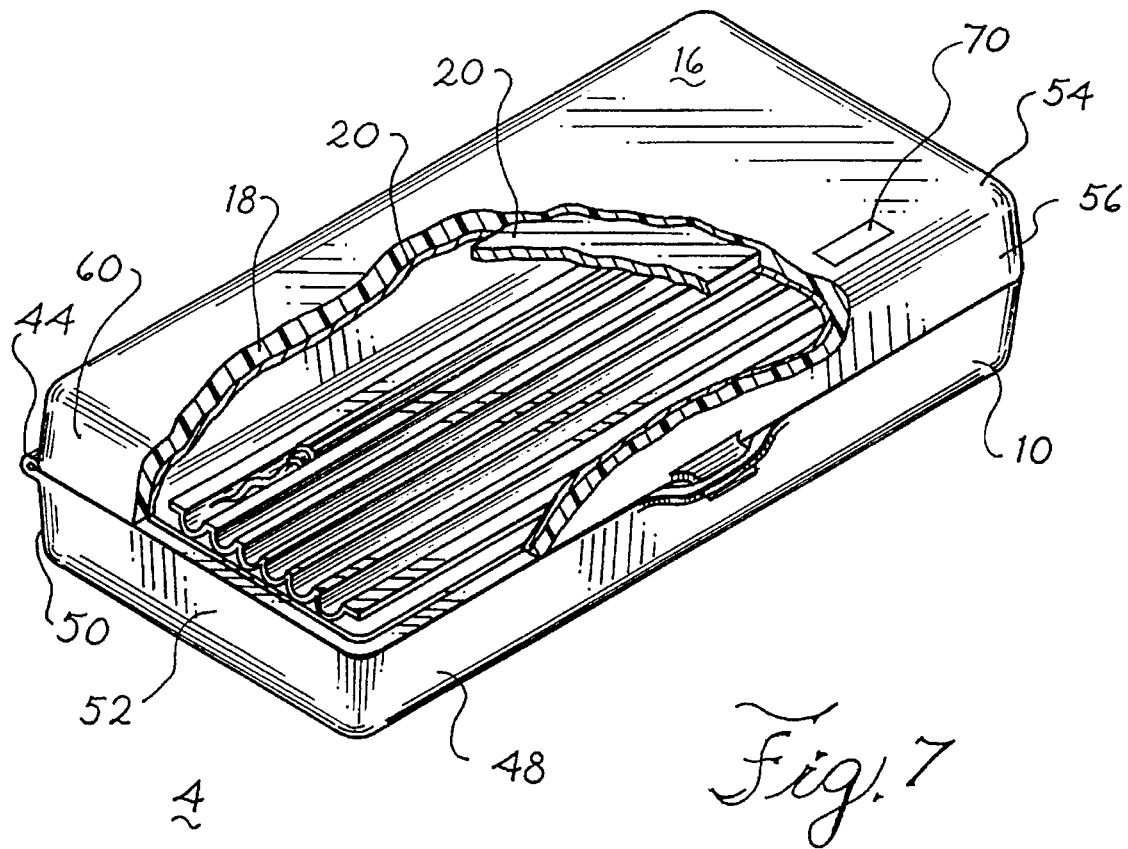
FIG. 7 shows a partially cut away view of the surgical instrument cassette of FIG. 6 when closed.
Figure 5:
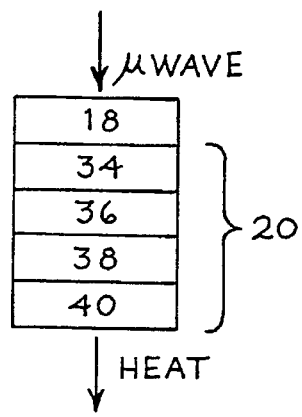
FIG. 5 shows a second embodiment of the layered structure of the inner surface for the surgical instrument bag of FIG. 2.
Figure 6:
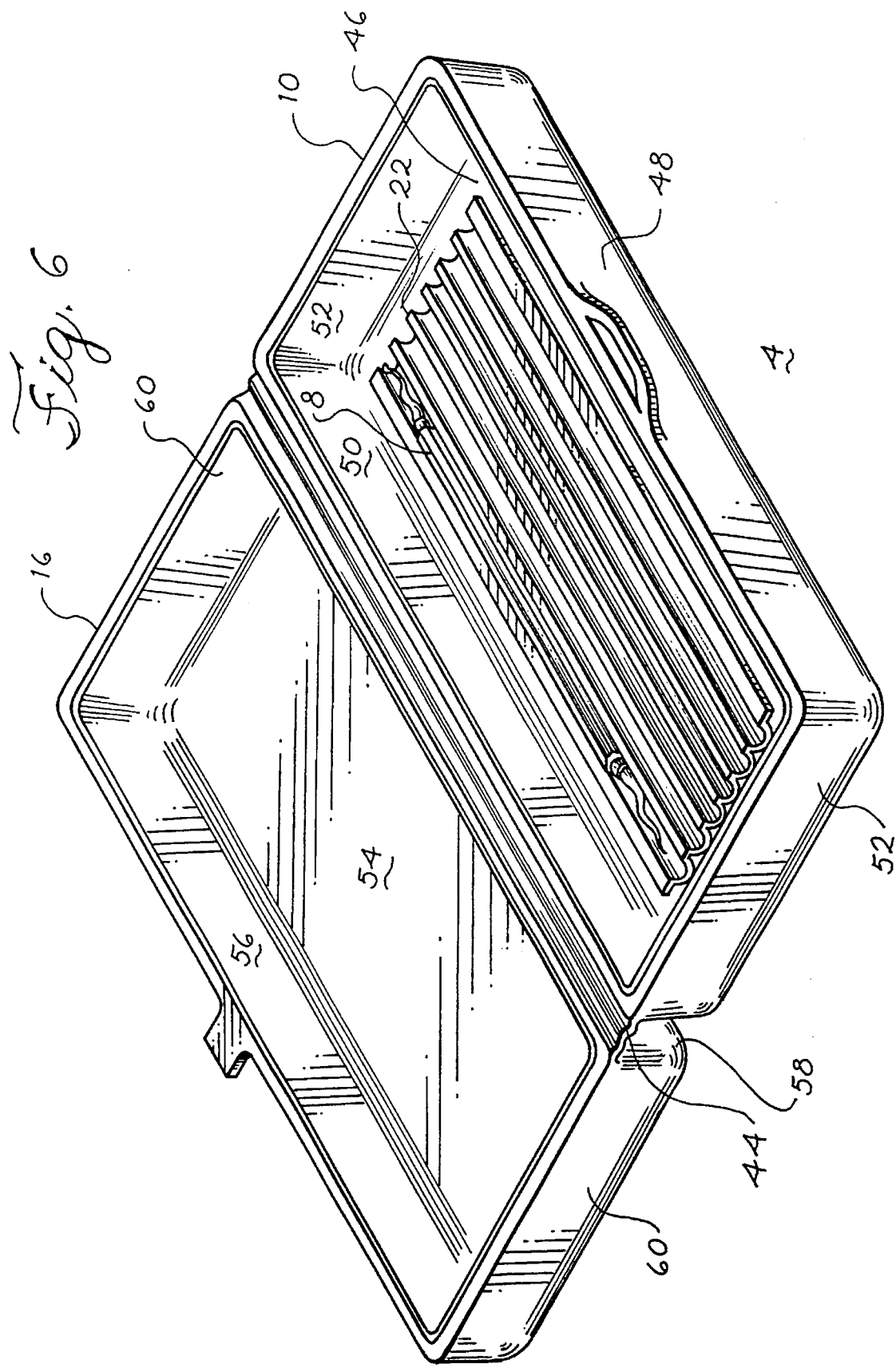
FIG. 6 shows the surgical instrument cassette of FIG. 1 when open.

Another way that arcing of the instruments 8 is lessened is by having at least one inner surface of either the surgical bag 2 of FIGS. 2–3 and the surgical cassette 4 of FIGS. 5–7 absorb substantially all of the microwave radiation that impinges on the exterior surfaces 12 and 18 and converting the absorbed microwave radiation into radiant heat energy that enters the volume of space and sterilizes the instruments 8.

In the embodiment of FIG. 3, the conversion of emitted microwave radiation to radiant heat with minimal transmission of microwaves is accomplished via inner surface 20 which comprises multi-layers of susceptor materials. Inner surface 20 is also known as a microwave-to-heat transducer. A cross-section of an embodiment of inner surface 20 is shown in FIG. 4.

Figure 4:
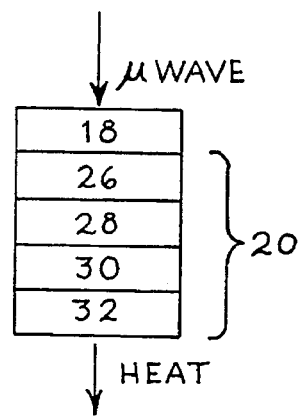
FIG. 4 shows a first embodiment of the layered structure of the inner surface for the surgical instrument bag of FIG. 2.

In FIG. 4, inner surface 20 comprises an adhesive 26 that attaches exterior surface 18 to susceptor material 28. Susceptor material 28 is well known and typically comprises a thin plastic layer with a plurality of metal (such as aluminum) conductive islands vacuum deposited therein. Examples of suitable susceptor materials are those known by the names of (1) Accu●Crisp made by A. D. Tech of Tauton, Mass.; and (2) Microcrisp by James River Corp. of Mentor, Ohio. Furthermore, adhesive 26 may comprise copolymers of EVA (ethylenevinylacetate), acrylics or urethane which are available from such companies as Swift Adhesives of Downers Grove, Ill. and H. B. Fuller Company of St. Paul, Minn.

As is well known, susceptor material 28 converts microwave radiation that impinges thereon to radiant heat. However, susceptor material 28 typically does not convert all of the microwave radiation into heat, but allows a fraction of the microwaves to be transmitted therethrough. It has been found that the transmitted microwaves are of an amount that is sufficient to cause arcing between metallic objects such as medical instruments 8.

To prevent the transmitted microwaves from causing arcing, a second material 32 is placed within inner surface 20 to substantially absorb the transmitted microwaves. Material 32 comprises either a second susceptor material or ferrite or iron oxide which is bonded to the first susceptor material 28 by a bonding layer 30 which preferably is made of a flexible, high temperature plastic, such as polyester or high temperature paper. The second material 32 may cover one or more sections of inner surface 20 or may cover the entire inner surface 20. Material 32 substantially absorbs the microwaves transmitted through susceptor material 28. Combining two or more microwave materials, such as susceptors and/or ferrites, it is possible to achieve both high temperatures within the interior and minimize the magnitude of the electric field therein so as to prevent arcing. In the layered structure of FIG. 4, each of the layers 18, 26, 28, 30 and 32 has a thickness ranging from approximately 0.1–25 mils, preferably 1 to 10 mils.

Regarding bottom 10, exterior surface or layer 12 preferably is made of paper or plastic and support surface 14 preferably comprises the same multilayer structure as shown in FIG. 4.

A second embodiment for the microwave-to-heat transducer of inner surface 20 and/or support surface 14 is shown by the cross-sectional view of FIG. 5. In FIG. 5, inner surface 20 comprises an adhesive 34 that attaches exterior surface 18 to a magnetic susceptor material 36. Adhesive 34 preferably is silicone or epoxy. Magnetic susceptor material 36 is similar to that of susceptor material 28 described above where the metal is replaced by magnetic material such as a ferrite or iron oxide.

Magnetic susceptor material 36 converts microwave radiation that impinges thereon to radiant heat. Those microwaves that are transmitted through layer 36 are reflected back by a metal layer 40 such as aluminum. Metal layer 40 is attached to magnetic susceptor material 36 by an adhesive layer 38 comprising silicone or epoxy. In the layered structure of FIG. 5, each of the layers 18, 34, 36, 38 and 40 has a thickness ranging from approximately 0.1–50 mils, preferably 1 to 20 mils. It should be kept in mind that layers 26 and 30 of FIG. 4 and layers 34 and 38 of FIG. 5 preferably are glued together in a laminate so as to form a single sheet of material from which bag 2 is formed.

With the surgical bag 2 described above, one sterilizes one or more surgical instruments 8 by inserting each instrument 8 through the opening and into the interior volume of space of the bag 2. Each instrument 8 preferably is placed in one of the channels 24 of tray 22 to prevent arcing between adjacent instruments 8. Once placed within bag 2, the opening is closed with a sealer such as an adhesive 42 or a heat seal. The sealer hermetically closes the instrument 8 within the volume of space so that the environment is not contaminated by viruses or the like within the volume of space. Furthermore, the instruments 8 preferably are exposed to a dry environment within the sealed volume of space.

At this point in time the bag 2 is placed within oven 6 and is exposed to microwave radiation from a microwave radiation source such as microwave oven 6 as shown in FIG. 1. The bag 2 may be rotated within oven 6 in a well known manner. For the purpose of this application, microwaves are considered to be electromagnetic radiation having a frequency ranging from approximately $10^6$ Hz to approximately $3 \times 10^{11}$ Hz. It is preferred that the frequency of the microwaves is approximately 2,450 MHz, the frequency of most commercial microwave ovens.

The microwave radiation impinges on susceptor material of inner surface 20 resulting in the production of radiant heat energy and attenuated microwave energy. The attenuated microwave energy then exposes the microwave material, such as a second susceptor material such as a ferrite or iron oxide, of inner surface 20 to convert substantially all of the attenuated microwave radiation to further radiant thermal energy within the volume of space containing the surgical instruments 8. The amount of radiant thermal energy produced by inner layer 20 and/or other layers defining the inner space that exposes the surgical instrument 8 is sufficient to sterilize the surgical instrument.

Sterilization of one or more instruments 8 may also be accomplished by opening cassette 4 and placing the instrument 8 in a channel 24 of tray 22 placed on bottom surface, as shown in FIG. 6. Furthermore, the instrument 8 may be placed in a hermetically sealed plastic pouch when placed in cassette 4. The cassette 4 preferably is box-like in shape having a bottom 10 and a top 16 attached to the bottom 10 by a hinge 44. Bottom 10 preferably has a bottom support surface 46 attached to a vertical front wall 48, a vertical back wall 50 and a pair of vertical side walls 52. Top 16 has a shape similar to that of bottom 10 in that top 16 has a top surface 54, a from wall 56, a back wall 58 and a pair of side walls 60.

The top 16 pivots about the hinge 44 from an open position as shown in FIG. 6 to a closed and hermetically sealed position as shown in FIG. 7. In the closed position, the top 16 and bottom 10 enclose a volume of space that contains one or more metallic surgical instruments 8.

As seen in FIG. 7, the top 16, including top surface 54, front wall 56, back wall 58 and side walls 50, preferably has a two layer structure with an exterior layer 18 made of plastic and, like bag 2, an inner layer 20. In one embodiment, inner layer 20 comprises the microwave-to-heat transducer described previously with respect to FIG. 4 that absorbs substantially all microwave radiation transmitted through the plastic exterior layer 18 and converts the absorbed microwave radiation to radiant heat energy. The amount of radiant heat energy produced by the inner layer 20 and transmitted to the volume of space is sufficient to sterilize the surgical instrument 8. The bottom 10, including bottom support surface 46 and walls 48, 50 and 52 may also comprise the two layer structure of top 16 described above. The microwave-to-heat transducer of the top 16 and bottom 10 is positioned closer to the volume of space containing the instruments 8 than the plastic exterior layer 18.

A second embodiment of inner layer 20 of cassette 4 is to use the microwave-to-heat transducer as described above with respect to FIG. 5. Of course, bottom 10, including bottom support surface 46 and walls 48, 50 and 52 can have the two layer structure of top 16 described above.

Figure 8:
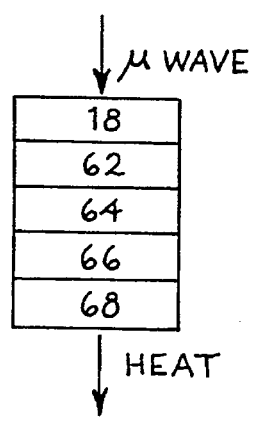
FIG. 8 shows an embodiment of the layered structure of the inner surface for the surgical instrument cassette of FIG. 6.

A third embodiment of a microwave-to-heat transducer for inner layer 20 of cassette 4 is to use the layered structure shown in FIG. 8. In FIG. 8, inner surface 20 comprises an adhesive 62, such as silicone or epoxy, that attaches exterior surface 18 to a ferrite material 64. Ferrite material 64 preferably contains a high concentration of a ferrite, such as iron oxide, embedded within silicon rubber or a high temperature epoxy. The concentration of ferrite material 64 ranges from approximately 10–99% by weight, preferably 30–90% by weight. The ferrite material 64 is then attached to a microwave reflective material, such as a metal 68 like aluminum. Attachment between materials 64 and 68 is accomplished via bonding layer 66 which may comprise silicon rubber.

The unique properties of the combination of ferrite material 64 near metal 68 are taken advantage of for heating the metal instruments to a predetermined temperature and preventing the metal instruments from being overly exposed to microwaves so as to cause arcing. Initially, microwaves impinge on ferrite material 62. Since microwaves are electromagnetic energy, they have both an electric field and magnetic field that can produce heat. However, metal 68 causes the electric field component to be reflected away from the volume of space while maximizing the magnetic field at the surface of metal 68. The reflection of the electric field prevents arcing within the volume of space while the magnetic field at the surface starts to produce heat which enters the volume of space so as to sterilize the instruments. The temperature of the ferrite material 62 continues to rise until it reaches its Curie point and heating is discontinued. Since the main object of the present invention is to sterilize surgical instruments, the ferrite material 62 preferably has a Curie point ranging from about 300° F. to about 350° F. Of course other Curie points may be chosen depending on the purpose of using microwaves, such as treating materials or cooking food. In the layered structure of FIG. 8, each of the layers 18, 62, 64, 66 and 68 has a thickness ranging from approximately 0.1–50 mils, preferably 1 to 20 mils.

Regarding bottom 10, exterior surface or layer 12 preferably is made of paper or plastic and support surface 14 preferably comprises the same multilayer structure as shown in FIG. 4. In addition, bottom 10 may be made of a microwave reflective material, such as aluminum.

For all of the embodiments of the bag 2 and cassette 4 it is possible to monitor the temperature within the volume of space containing the instrument 8. For example, a temperature sensitive label 70 may be placed on the exterior surface of the bag 2 or cassette 4. The label 70 would either change color or reveal certain indicia, such as the words "Sterilization" or "Sterilized," upon attainment of a predetermined temperature within the volume of space. Examples of suitable labels are available under the name of WaveRite™ and manufactured by LifeLines Technology, Inc. of Morris Plains, N.J.

Once the indicia changes color or reveals the indicia it indicates that the instruments have been sterilized. Typically, sterilization occurs by exposing the instruments to temperatures ranging from about 300° F. to about 350° F. for approximately 2 to 6 minutes. Upon sterilization, the instruments are then removed from the containers and placed in sterile pouches or the like and stored until they are needed.

In addition, a temperature control material, such as the material known by the name Safety Susceptor™ made by A. D. Tech may be attached to the inner most layers of the microwave-to-heat transducers shown in FIGS. 4 and 5. The temperature control material is placed nearest the volume of space and acts as a fuse in that it shuts off further electromagnetic energy from entering the volume of space once a predetermined temperature is reached within the volume of space.

The foregoing description is provided to illustrate the invention, and is not to be construed as a limitation. Numerous additions, substitutions and other changes can be made to the invention without departing from its scope as set forth in the appended claims. For example, bag 2 and cassette 4 may be used for other purposes, such as (1) containing and treating metallic materials with microwave radiation and (2) containing and cooking food items within a metallic vessel, like a pot or pan.

In addition, while the above description has in general had the microwaves entering through the top surface and interacting with the microwave-to-heat transducer, it is possible for microwaves to enter through the bottom surface as well. In such a case, it is possible to reverse the roles of the top and bottom surfaces as described previously and have the microwave-to-heat transducers of FIGS. 4, 5 and 8 at the bottom surface and have a metal microwave reflectant material for the top surface.

We claim:

1. A method of sterilizing a metallic object with microwaves while preventing arcing of the metallic object, said method comprising the steps of:

placing said metallic object within a volume of space defined by a surface of material, wherein said surface comprises a microwave-to-heat transducer that comprises a first susceptor material and a microwave absorbing material positioned between said first susceptor material and said volume of space;

exposing said surface of material to microwave radiation;

converting a portion of said microwave radiation exposing said surface of material to radiant thermal energy within said volume of space;

exposing said metallic object to said radiant thermal energy in an amount sufficient to sterilize said metallic object; and preventing substantially all of said microwave radiation impinging on said surface of material from entering said volume of space.

2. The method of claim 1, wherein said metallic object is either a surgical instrument or a dental instrument.

3. The method of claim 1, said step of converting comprises exposing said first susceptor to said microwaves to produce heat; and exposing said microwave absorbing material to microwaves transmitted through said first susceptor to produce further heat;

said preventing step comprises said microwave absorbing material absorbing substantially all of said microwaves transmitted through said first susceptor.

4. The method of claim 3, wherein said microwave absorbing material comprises a second susceptor material.

5. The method of claim 3, wherein said microwave absorbing material comprises a magnetic material.

6. The method of claim 5, wherein said magnetic material comprises a ferrite.

7. The method of claim 6, wherein said ferrite is a magnetic susceptor.

8. The method of claim 1, comprising the step of hermetically sealing said volume of space.

9. The method of claim 8, wherein said volume of space defines a dry environment.

10. The method of claim 1, comprising the step of placing a tray containing said surgical instrument within said volume of space.

11. The method of claim 10, comprising the step of a hermetically sealing said volume of space wherein said surgical instrument is located.

12. The method of claim 11, wherein said volume of space defines a dry environment.

13. The method of claim 1, wherein said metallic object is stationary during the step of exposing the material to microwaves.

14. The method of claim 1, comprising the steps of:

placing a second metallic object within said volume of space in which said metallic object is present;

exposing said second metallic object to said radiant thermal energy in an amount sufficient to sterilize said second metallic object;

wherein the amount of microwave radiation entering said volume of space is insufficient to cause arcing of the metallic object or the second metallic object.

15. The method of claim 1, wherein the amount of microwave radiation entering said volume of space is insufficient to cause arcing of said metallic object.

* * * * *